(12) United States Patent
Yamada et al.

(10) Patent No.: US 8,021,767 B2
(45) Date of Patent: Sep. 20, 2011

(54) 4-ARYLFLUORENE COMPOUND AND ORGANIC LIGHT-EMITTING DEVICE USING SAME

(75) Inventors: Naoki Yamada, Inagi (JP); Akihito Saitoh, Yokohama (JP); Jun Kamatani, Tokyo (JP); Satoshi Igawa, Fujisawa (JP); Shinjiro Okada, Kamakura (JP)

(73) Assignee: Canon Kabushiki Kaisha, Tokyo (JP)

( * ) Notice: Subject to any disclaimer, the term of this patent is extended or adjusted under 35 U.S.C. 154(b) by 543 days.

(21) Appl. No.: 12/298,749

(22) PCT Filed: Apr. 12, 2007

(86) PCT No.: PCT/JP2007/058476
§ 371 (c)(1),
(2), (4) Date: Oct. 27, 2008

(87) PCT Pub. No.: WO2007/125809
PCT Pub. Date: Nov. 8, 2007

(65) Prior Publication Data
US 2009/0134788 A1    May 28, 2009

(30) Foreign Application Priority Data

Apr. 27, 2006  (JP) .................................. 2006-123784
Nov. 16, 2006  (JP) .................................. 2006-310380

(51) Int. Cl.
*H01L 51/54* (2006.01)
(52) U.S. Cl. ........ 428/690; 428/917; 313/504; 313/505; 313/506; 570/129
(58) Field of Classification Search .................. 428/690, 428/917; 313/504, 505, 506; 570/129
See application file for complete search history.

(56) References Cited

U.S. PATENT DOCUMENTS

| 7,097,917 | B1 | 8/2006 | Fujita et al. ................... 428/690 |
| 2003/0087126 | A1 | 5/2003 | Ishida et al. .................. 428/690 |
| 2004/0253389 | A1* | 12/2004 | Suzuki et al. .................. 428/1.1 |
| 2005/0074631 | A1 | 4/2005 | Ishida et al. .................. 428/690 |
| 2005/0236974 | A1 | 10/2005 | Suzuki et al. ................. 313/504 |
| 2005/0236977 | A1 | 10/2005 | Yamada et al. ............... 313/504 |

(Continued)

FOREIGN PATENT DOCUMENTS
JP          11-185960          7/1999
(Continued)

OTHER PUBLICATIONS

Yang et al., "Synthesis and Rotational Barriers of Atropisomers of 1,2-bis[5-(11*H*-benzo[*b*]fluoreny)]benzenes and Related Compounds," *Tetrahedron*, vol. 62, 1231-1238 (2006).

(Continued)

*Primary Examiner* — D. Lawrence Tarazano
*Assistant Examiner* — Gregory Clark
(74) *Attorney, Agent, or Firm* — Fitzpatrick, Cella, Harper & Scinto

(57) ABSTRACT

The present invention provides a high-performance organic light-emitting device, and a novel organic compound for use in the device. The novel compound of the present invention is a 4-arylfluorene compound having a specific structure. The organic light-emitting device of the present invention is an organic light-emitting device including: a pair of electrodes comprising an anode and a cathode; and an organic compound layer interposed between the pair of electrodes, wherein the organic compound layer contains the 4-arylfluorene compound.

6 Claims, 5 Drawing Sheets

U.S. PATENT DOCUMENTS

| | | | |
|---|---|---|---|
| 2006/0113528 A1 | 6/2006 | Okinaka et al. | 257/40 |
| 2007/0111029 A1 | 5/2007 | Yamada et al. | 428/690 |
| 2007/0152565 A1 | 7/2007 | Kubota et al. | 313/504 |
| 2008/0124577 A1 | 5/2008 | Saitoh et al. | 428/704 |
| 2008/0224603 A1 | 9/2008 | Hashimoto et al. | 313/504 |
| 2008/0272692 A1 | 11/2008 | Hashimoto et al. | 313/504 |
| 2008/0286611 A1 | 11/2008 | Muratsubaki et al. | 428/704 |

FOREIGN PATENT DOCUMENTS

| | | |
|---|---|---|
| JP | 11-204262 | 7/1999 |
| JP | 11-288783 | 10/1999 |
| JP | 2002-069044 | 3/2002 |
| JP | 2002-154993 | 5/2002 |
| JP | 2004-043349 | 2/2004 |
| JP | 2004-083481 | 3/2004 |
| JP | 2004-107326 | 4/2004 |
| JP | 2005-239650 | 9/2005 |
| JP | 2005-240008 | 9/2005 |
| WO | 02/085822 A1 | 10/2002 |
| WO | 2005/061656 | 7/2005 |
| WO | 2007/039344 A2 | 4/2007 |
| WO | WO 2007/114038 A1 | 10/2007 |

OTHER PUBLICATIONS

*Chemical Abstracts,* vol. 61, No. 14649b-d (Rn=857025-09-3, (1964).

*Chemical Abstracts,* vol. 57, Nos. 747i, 748a-i, 749a, (1962).

European Search Report dated Mar. 24, 2009.

* cited by examiner

4-ARYLFLUORENE COMPOUND AND ORGANIC LIGHT-EMITTING DEVICE USING SAME

TECHNICAL FIELD

The present invention relates to a novel 4-arylfluorene compound and an organic light-emitting device using the same.

BACKGROUND ART

An organic light-emitting device includes: an anode; a cathode; and a thin film containing a fluorescent organic compound or a phosphorescent organic compound, the thin film being interposed between the anode and the cathode. An electron and a hole are injected from the respective electrodes to the thin film.

Further, the organic light-emitting device generates an exciton of the fluorescent organic compound or of the phosphorescent organic compound. The device utilizes light to be radiated when the exciton returns to its ground state.

Recent progress in an organic light-emitting device is remarkable. There are characteristics capable of producing a thin, lightweight organic light-emitting device having high luminance at a low applied voltage, various emission wavelengths and high-speed responsiveness. Therefore, these characteristics suggest that the light emitting device may be used in a wide variety of applications.

However, the conventional organic light-emitting device requires optical output with higher luminance or higher conversion efficiency. In addition, the organic light-emitting device still involves many problems in terms of durability such as a change with elapse of time due to long-term use and deterioration due to, for example, an atmospheric gas containing oxygen or humidity.

Further, when it is attempted that the device is applied to a full-color display and the like, blue light, green light, and red light must be emitted at a good color purity. However, problems concerning the emission have not been sufficiently solved yet.

In addition, the examples of a material and an organic light-emitting device using a fluorene compound are disclosed in Japanese Patent Application Laid-Open Nos. H11-288783, H11-185960, H11-204262, 2002-154993, 2004-043349, and 2005-239650. However, the devices disclosed in those applications have a low emission efficiency and an insufficient durable lifetime. In addition, some of the applications describe nothing about a durable lifetime.

DISCLOSURE OF THE INVENTION

An object of the present invention is to provide a novel 4-arylfluorene compound.

Another object of the present invention is to provide an organic light-emitting device using the 4-arylfluorene compound and having an optical output with extremely high efficiency and extremely high luminance. Another object of the present invention is to provide an organic light-emitting device having extremely high durability.

Another object of the present invention is to provide an organic light-emitting device that can be easily produced at a relatively low cost.

According to the present invention, there is provided a 4-arylfluorene compound represented by the following general formula (I):

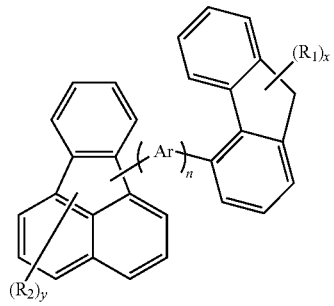

wherein: n represents an integer of 0 to 10; when n represents 0, Ar represents a direct bond between a fluorene group and a fluoranthene group; when n represents an integer of 1 to 10, Ar represents a substituted or unsubstituted, divalent alkylene group, a substituted or unsubstituted, divalent aralkylene group, a substituted or unsubstituted, divalent arylene group, or a substituted or unsubstituted, divalent heterocyclic group; when n represents an integer of 1 to 10, Ar's may be the same as or different from each other; $R_1$ and $R_2$ each represent a substituted or unsubstituted alkyl group, a substituted or unsubstituted aralkyl group, a substituted or unsubstituted alkoxy group, a substituted or unsubstituted aryl group, a substituted or unsubstituted heterocyclic group, a substituted or unsubstituted amino group, a cyano group, or a halogen group, and $R_1$ and $R_2$ may be the same as or different from each other; x and y each represent an integer of 0 to 9; and when x or y represents an integer of 2 or more, $R_1$'s or $R_2$'s may be the same as or different from each other, or $R_1$'s or $R_2$'s may be bonded to each other to form a ring.

The 4-arylfluorene compound represented by the general formula (I) of the present invention has good film formability, and emits blue light having an excellent color purity. In addition, an organic light-emitting device using the 4-arylfluorene compound emits light with high efficiency at a low applied voltage.

Further features of the present invention will become apparent from the following description of exemplary embodiments with reference to the attached drawings.

BEST MODE FOR CARRYING OUT THE INVENTION

Figure 1:
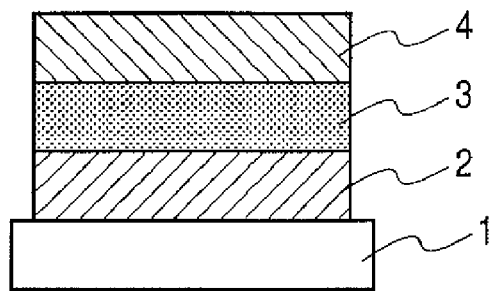
FIG. 1 is a sectional view showing an example of an organic light-emitting device in the present invention.

According to the present invention, there is provided a 4-arylfluorene compound represented by the following general formula (I):

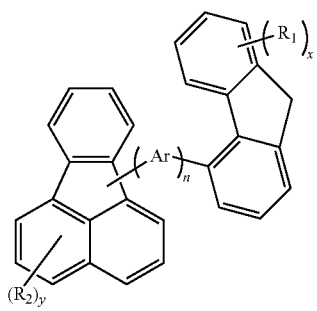

(I)

wherein n represents an integer of 0 to 10; when n represents 0, Ar represents a direct bond between a fluorene group and a fluoranthene group; when n represents an integer of 1 to 10, Ar represents a substituted or unsubstituted, divalent alkylene group, a substituted or unsubstituted, divalent aralkylene group, a substituted or unsubstituted, divalent arylene group, or a substituted or unsubstituted, divalent heterocyclic group; when n represents an integer of 1 to 10, Ar's may be the same as or different from each other; $R_1$ and $R_2$ each represent a substituted or unsubstituted alkyl group, a substituted or unsubstituted aralkyl group, a substituted or unsubstituted alkoxy group, a substituted or unsubstituted aryl group, a substituted or unsubstituted heterocyclic group, a substituted or unsubstituted amino group, a cyano group, or a halogen group, and $R_1$ and $R_2$ may be the same as or different from each other; x and y each represent an integer of 0 to 9; and when x or y represents an integer of 2 or more, $R_1$'s or $R_2$'s may be the same as or different from each other, or $R_1$'s or $R_2$'s may be bonded to each other to form a ring.

In addition, according to the present invention, there is provided a 4-arylfluorene compound, in which Ar in the general formula (I) represents a substituted or unsubstituted phenylene group.

In addition, according to the present invention, there is provided a 4-arylfluorene compound, in which n in the general formula (I) represents 0.

In addition, according to the present invention, there is provided a 4-arylfluorene compound, in which Ar in the general formula (I) represents a substituted or unsubstituted naphthalene group.

In addition, according to the present invention, there is provided a 4-arylfluorene compound, in which Ar in the general formula (I) represents a substituted or unsubstituted anthracene group.

Further, in addition, according to the present invention, there is provided an organic light-emitting device including: a pair of electrodes having an anode and a cathode; and an organic compound layer interposed between the pair of electrodes, in which the organic compound layer contains any one of the above-mentioned 4-arylfluorene compounds.

Further, in addition, according to the present invention, there is provided an organic light-emitting device in which the organic compound layer is a light-emitting layer.

Specific examples of the substituents of the compounds in the general formula (I) is shown above.

Examples of the alkyl group include a methyl group, an ethyl group, a normal propyl group, an isopropyl group, a normal butyl group, a tertiary butyl group, a secondary butyl group, an octyl group, a 1-adamantyl group, a 2-adamantyl group, and the like.

Examples of the aralkyl group include a benzyl group and a phenethyl group.

Examples of the alkoxy group include a methoxy group, an ethoxy group, a propoxy group, and a phenoxy group.

Examples of the aryl group include a phenyl group, a naphthyl group, a pentalenyl group, an indenyl group, an azulenyl group, an anthryl group, a pyrenyl group, an indacenyl group, an acenaphthenyl group, a phenanthryl group, a phenalenyl group, a fluoranthenyl group, an acephenanthyl group, an aceanthryl group, a triphenylenyl group, a chrysenyl group, a naphthacenyl group, a perylenyl group, a pentacenyl group, a biphenyl group, a terphenyl group, and a fluorenyl group.

Examples of the heterocyclic group include a thienyl group, a pyrrolyl group, a pyridyl group, an oxazolyl group, an oxadiazolyl group, a thiazolyl group, a thiadiazolyl group, a terthienyl group, a carbazolyl group, an acridinyl group, a phenanthroyl group, and the like.

Examples of the halogen atom include fluorine, chlorine, bromine, iodine, and the like.

Examples of the amino group include a dimethylamino group, a diethylamino group, a dibenzylamino group, a diphenylamino group, a ditolylamino group, a dianisolylamino group, and the like.

Examples of substituents which the above-mentioned substituents may have include: alkyl groups such as a methyl group, an ethyl group, and a propyl group; aralkyl groups such as a benzyl group and a phenethyl group; aryl groups such as a phenyl group and a biphenyl group; heterocyclic groups such as a thienyl group, a pyrrolyl group, and a pyridyl group; amino groups such as a dimethylamino group, a diethylamino group, a dibenzylamino group, a diphenylamino group, a ditolylamino group, and a dianisolylamino group; alkoxyl groups such as a methoxyl group, an ethoxyl group, a propoxyl group, and a phenoxyl group; a cyano group; a cyano group; and halogen atoms such as fluorine, chlorine, bromine, and iodine.

The 4-arylfluorene compound represented by the general formula (I) can be used as a material for an organic light-emitting device.

In the device, the 4-arylfluorene compound represented by the general formula (I) can be used in each of a hole transport layer, an electron transport layer, and a light-emitting layer. As a result, a device having high emission efficiency and a long lifetime can be obtained.

In addition, when the 4-arylfluorene compound represented by the general formula (I) is used in a light-emitting layer, a device having a high color purity, high emission efficiency, and a long lifetime can be obtained by using the compound according to any one of various modes.

For example, the compound can be used alone or as a host material for each of a dopant (guest) material, a fluorescent material, and a phosphorescent material in a light-emitting layer. As a result, a device having a high color purity, high emission efficiency, and a long lifetime can be obtained.

In the 4-arylfluorene compound represented by the general formula (I), 4-position of the fluorene group is substituted with an aryl group. The substitution enables the entire molecule of the compound to be designed in a non-planar structure. As a result, a molecule having high amorphous property can be provided, and hence a device having high thermal stability and a long lifetime can be obtained. In addition, the non-planar molecular structure of the 4-arylfluorene compound represented by the general formula (I) reduces molecular association to suppress the emission of light having a long wavelength due to the association, so the compound is useful as a blue light-emitting material. In addition, the introduction of a substituent into the fluoranthene group can provide a good green or red light-emitting material.

Further, replacing an Ar group in the 4-arylfluorene compound represented by the general formula (I) with a direct bond or a phenyl group widens the band gap of the entire molecule of the compound, whereby the compound becomes useful as a blue light-emitting material. In addition, replacing the Ar group with a fused polycyclic group such as an anthracenyl group or a fluorenyl group narrows the band gap of the entire molecule of the compound, whereby the compound becomes useful as a green or red light-emitting material.

Further, the fluorene group, or the fluoranthene group substituted by any other aryl group can provide a device having high emission efficiency because such groups have high emission efficiency.

The HOMO/LUMO level of the 4-arylfluorene compound represented by the general formula (I) can be easily adjusted by introducing a substituent into the fluorene group or the fluoranthene group.

Accordingly, a molecule of the compound can be easily designed while a carrier injection balance between a hole and an electron is taken into consideration.

The present invention has been made as a result of molecular design based on such discussion as described above.

Hereinafter, the present invention will be described in more detail.

Specific examples of the compound represented by the above general formula (I) are shown below. However, the present invention is not limited to these examples.

In Table 1, the compound to be used in the present invention is represented by A-B-C, and B represents the position to which A and C are bonded. That is, Exemplified Compound 9 is represented as described below. Although the letter B is not shown in a fluorene group represented by A, 4-position of the group represented by A is substituted by an aryl group (B). For easier understanding, a bonding hand is shown at 4-position of the fluorene group A in A in each of the following formulae and Table 1.

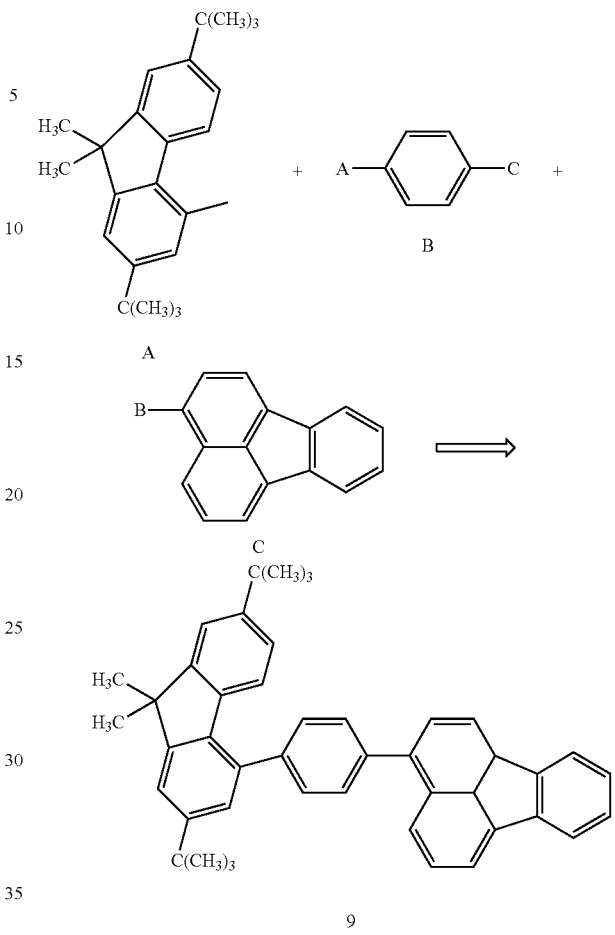

TABLE 1

| Compound No | A | B | C |
|---|---|---|---|
| 1 | (9,9-dimethyl-4-methylfluorenyl) | Direct bond | (fluoranthenyl) |
| 2 | (9,9-dimethyl-4-methylfluorenyl) | Direct bond | (bis-isopropyl fluoranthenyl) |

TABLE 1-continued

| Compound No | A | B | C |
|---|---|---|---|
| 3 | [9,9-dimethyl-2,7-di-tert-butyl-4-methylfluorene] | Direct bond | [methyl-substituted fluoranthene fused with naphthalene] |
| 4 | [9,9-dimethyl-2,7-di-tert-butyl-4-methylfluorene] | Direct bond | [methyl-substituted fluoranthene] |
| 5 | [9,9-dimethyl-2,7-di-tert-butyl-4-methylfluorene] | Direct bond | [methyl-substituted diphenyl-fluoranthene fused with naphthalene] |
| 6 | [9,9-dimethyl-2,7-di-tert-butyl-4-methylfluorene] | Direct bond | [methyl-substituted di-isopropyl-fluoranthene] |
| 7 | [9,9-dimethyl-2,7-di-tert-butyl-4-methylfluorene] | Direct bond | [methyl-substituted diphenyl-fluoranthene] |
| 8 | [9,9-diphenyl-2,7-di-tert-butyl-4-methylfluorene] | Direct bond | [methyl-substituted fluoranthene] |

TABLE 1-continued

| Compound No | A | B | C |
|---|---|---|---|
| 9 | 2,7-di-tert-butyl-4,9,9-trimethyl-9H-fluorene | 1,4-phenylene | methyl-fluoranthene |
| 10 | 2,7-di-tert-butyl-4,9,9-trimethyl-9H-fluorene | 1,4-phenylene | methyl-fluoranthene (isomer) |
| 11 | 2,7-di-tert-butyl-4,9,9-trimethyl-9H-fluorene | 1,4-phenylene | diphenyl-substituted methyl-fluoranthene |
| 12 | 2,7-di-tert-butyl-4,9,9-trimethyl-9H-fluorene | 5-methyl-1,3-phenylene | diisopropyl-substituted methyl-fluoranthene |
| 13 | 2,7-di-tert-butyl-4,9,9-trimethyl-9H-fluorene | 1,3-phenylene | diphenyl-substituted methyl-fluoranthene |
| 14 | 2,7-di-tert-butyl-4,9,9-trimethyl-9H-fluorene | 4,4'-biphenylene | methyl-fluoranthene |

TABLE 1-continued
| Compound No | A | B | C |
|---|---|---|---|
| 15 | 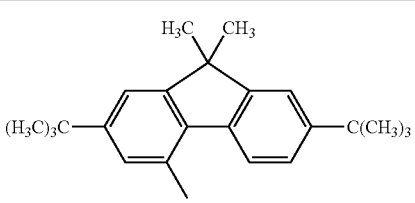 | 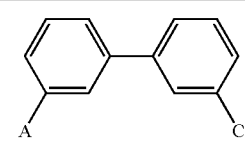 | 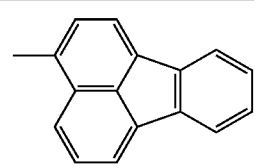 |
| 16 | 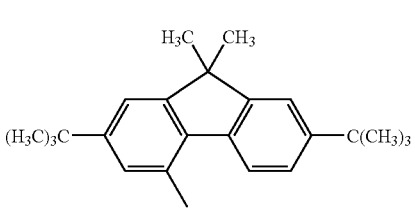 | 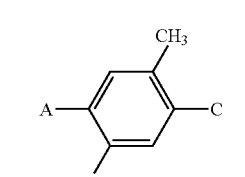 | 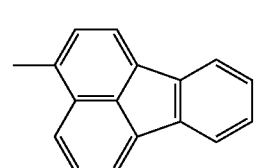 |
| 17 | 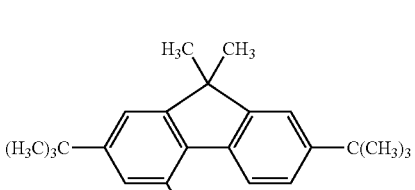 | 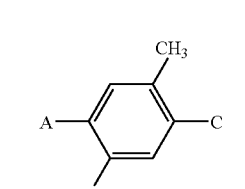 | 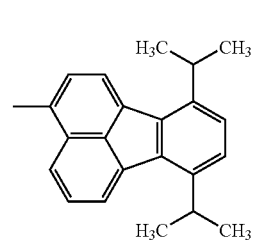 |
| 18 | 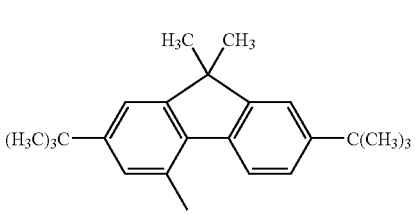 | 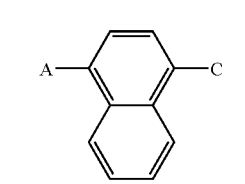 | 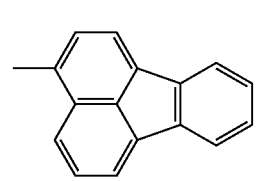 |
| 19 | 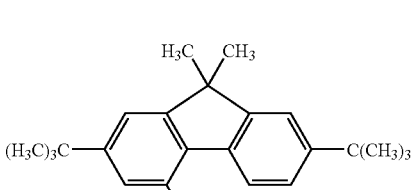 | 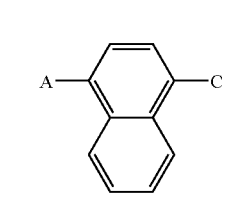 | 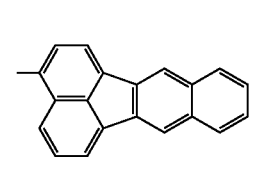 |
| 20 | 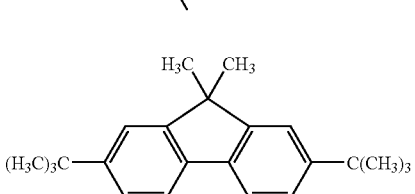 | 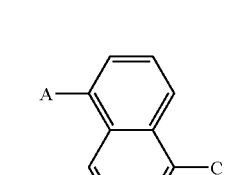 | 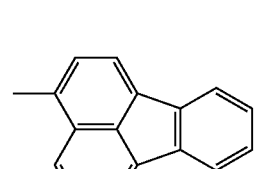 |
| 21 | 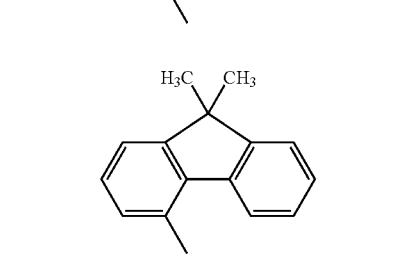 | 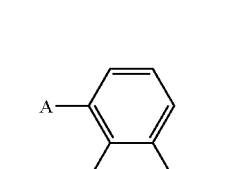 | 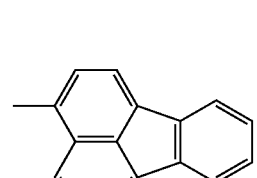 |

TABLE 1-continued

| Compound No | A | B | C |
|---|---|---|---|
| 22 | 2,7-di-tert-butyl-4,9,9-trimethylfluorene | 9,10-disubstituted anthracene (A,C) | methyl-fluoranthene |
| 23 | 9,9-dimethyl-4-methylfluorene | 9,10-disubstituted anthracene (A,C) | methyl-fluoranthene |
| 24 | 2,7-di-tert-butyl-4,9,9-trimethylfluorene | 9,10-disubstituted anthracene (A,C) | methyl-diphenyl-fluoranthene |
| 25 | 2,7-di-tert-butyl-4,9,9-trimethylfluorene | 9,10-disubstituted anthracene (A,C) | methyl-diphenyl-benzofluoranthene |
| 26 | 2,7-di-tert-butyl-4,9,9-trimethylfluorene | 9,10-disubstituted anthracene (A,C) | methyl-fluoranthene |
| 27 | 2,7-di-tert-butyl-4,9,9-trimethylfluorene | 2,7-disubstituted-9,9-dimethylfluorene (A,C) | methyl-fluoranthene |

TABLE 1-continued

| Compound No | A | B | C |
|---|---|---|---|
| 28 | | | |
| 29 | | | |
| 30 | | | |
| 31 | | | |
| 32 | | | |
| 33 | | | |
| 34 | | | |

TABLE 1-continued

| Compound No | A | B | C |
|---|---|---|---|
| 35 | | | |
| 36 | | | |
| 37 | | A-CH₂—C | |
| 38 | | A-CH₂—C | |

Next, an organic light-emitting device of the present invention will be described in detail.

The organic light-emitting device of the present invention includes: a pair of electrodes having an anode and a cathode; and one or more layers each containing an organic compound, the one or more layers being interposed between the pair of electrodes, wherein at least one layer of the one or more layers each containing an organic compound contains at least one kind of compounds represented by the general formula (I).

FIGS. 1, 2, 3, 4 and 5 each show a preferable example of the organic light-emitting device of the present invention.

FIG. 1 is a sectional view illustrating an example of an organic light-emitting device according to the present invention. As illustrated in FIG. 1, the organic light-emitting device has a structure in which the anode 2, the light-emitting layer 3, and the cathode 4 are provided on the substrate 1 in this order. The light-emitting device used herein is useful in the case where the light-emitting layer itself has hole-transporting property, electron-transporting property, and light-emitting property or where compounds having the respective properties are mixed and used in the light-emitting layer.

Figure 2:
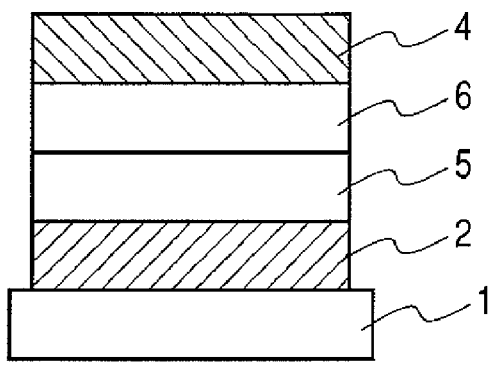
FIG. 2 is a sectional view showing another example of the organic light-emitting device in the present invention.

FIG. 2 is a sectional view illustrating another example of the organic light-emitting device according to the present invention. As illustrated in FIG. 2, the organic light-emitting device has a structure in which the anode 2, the hole transport layer 5, the electron transport layer 6, and the cathode 4 are provided on the substrate 1 in this order. A light-emitting substance is useful in the case where a material having one or both of hole-transporting property and electron-transporting property is used for each layer, and the light-emitting substance is used in combination with a hole-transporting substance or electron-transporting substance having no light-emitting property. In this case, the light-emitting layer is formed of the hole transport layer 5 or the electron transport layer 6.

Figure 3:
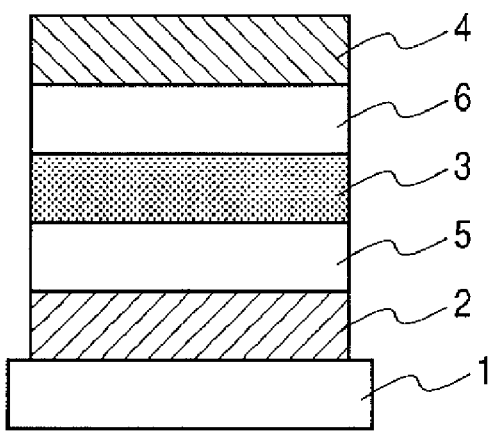
FIG. 3 is a sectional view showing another example of the organic light-emitting device in the present invention.

FIG. 3 is a sectional view illustrating still another example of the organic light-emitting device according to the present invention. As illustrated in FIG. 3, the organic light-emitting device has a structure in which the anode 2, the hole transport layer 5, the light-emitting layer 3, the electron transport layer 6, and the cathode 4 are provided on the substrate 1 in this order. This organic light-emitting device has separate carrier-transporting function and light-emitting function. The device is used in which compounds each having hole-transporting property, electron-transporting property, or light-emitting property are combined as appropriate, thereby allowing a substantial increase in freedom of choice in material to be used. Further, various compounds having different emission wavelengths can be used, thereby allowing an increase in variety of luminescent colors. Further, emission efficiency may be improved by efficiently trapping each carrier or exciton in the light-emitting layer 3 provided in the middle of the device.

Figure 4:
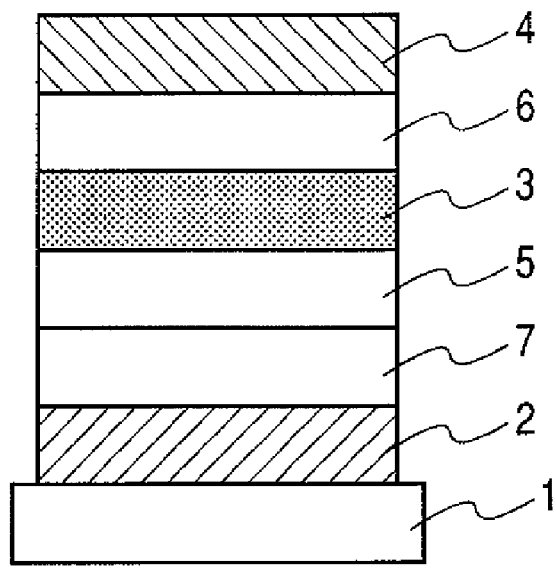
FIG. 4 is a sectional view showing another example of the organic light-emitting device in the present invention.

FIG. 4 is a sectional view illustrating yet another example of the organic light-emitting device according to the present invention. FIG. 4 has a structure illustrated in FIG. 3 except that a hole injection layer 7 is inserted into a side of the anode 2. This structure is effective for improving adhesiveness between the anode 2 and the hole transport layer 5 or for improving hole-injecting property, which is effective in lowering a voltage to be applied to the device.

Figure 5:
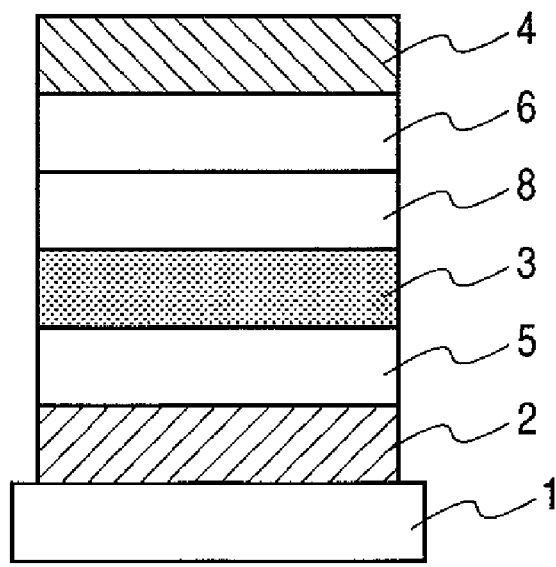
FIG. 5 is a sectional view showing another example of the organic light-emitting device in the present invention.

FIG. 5 is a sectional view illustrating still yet another example of the organic light-emitting device according to the present invention. FIG. 5 has a structure illustrated in FIG. 3 except that a layer (hole/exciton-blocking layer 8) for blocking travel of a hole or exciton to a side of the cathode 4 is inserted between the light-emitting layer 3 and the electron transport layer 6. In this structure, a compound having an extremely high ionization potential is used for the hole/exciton-blocking layer 8, and this structure is effective for improving emission efficiency.

FIGS. 1, 2, 3, 4 and 5 each illustrate a basic device structure, and the structure of the organic light-emitting device using the compound of the present invention is not limited to the structures illustrated in FIGS. 1, 2, 3, 4 and 5. For example, the organic light-emitting device of the present invention may have any one of various layer structures including: a structure in which an insulating layer is provided at an interface between an electrode and an organic layer; a structure in which an adhesive or interference layer is provided; and a structure in which a hole transport layer includes two layers with different ionization potentials.

The compound represented by the general formula (I) to be used in the present invention can be used in any one of the forms shown in FIGS. 1, 2, 3, 4 and 5.

In particular, an organic layer using the compound of the present invention is formed by, for example, a vacuum deposition method or a solution application method, hardly causes crystallization or the like, and is excellent in stability with elapse of time.

In the present invention, the compound represented by the general formula (I) is used particularly as a constituent for a light-emitting layer. A conventionally known low-molecular-weight-based or polymer-based hole transport compound, light-emitting compound, electron transport compound, or the like can be used together with the above compound of the present invention as required.

The substrate to be used in the present invention is not particularly limited, but examples thereof include: an opaque substrate such as a metallic substrate or a ceramics substrate; and a transparent substrate such as a glass substrate, a quartz substrate, or a plastic sheet substrate.

In addition, the substrate may have a color filter film, a fluorescent color converting filter film, a dielectric reflection film, or the like for controlling luminescent color. Further, a thin film transistor (TFT) may be produced on a substrate, and then the device of the present invention may be produced to be connected to TFT.

Regarding the emission direction of a device, the device may have a bottom emission structure (structure in which light is emitted from a substrate side) or a top emission structure (structure in which light is emitted from an opposite side of the substrate).

Hereinafter, the present invention will be described more specifically with reference to the following examples, but the present invention is not limited to the examples.

EXAMPLE 1

Synthesis of Exemplified Compound 4

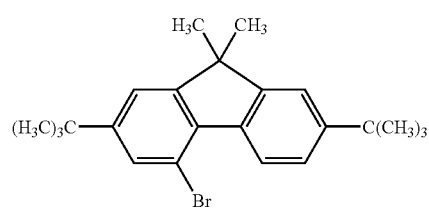

1-1

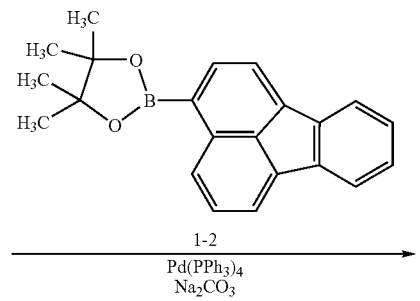

1-2
Pd(PPh$_3$)$_4$
Na$_2$CO$_3$

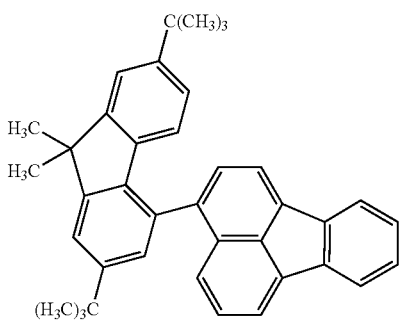

(a) Synthesis of Intermediate Compound 1-1

Intermediate Compound 1-1 can be produced by subjecting 2,7-ditertiarybutylfluorene (Sigma-Aldrich Corporation) as a raw material to dimethylation.

(b) Synthesis of Exemplified Compound 4

0.66 g (1.70 mmol) of Intermediate Compound 1-1, 0.656 g (2.00 mmol) of Compound 1-2, 120 ml of toluene, and 20 ml of ethanol were charged in a 200-ml three-necked flask, and the mixture was stirred under a nitrogen atmosphere at room temperature. During the stirring, an aqueous solution prepared by dissolving 10 g of sodium carbonate in 100 ml of water was dropped to the mixture, and then 0.20 g (0.170 mmol) of tetrakis(triphenylphosphine)palladium(0) was added to the mixture. The resultant was heated to 77° C., and was then stirred for 5 hours. After the reaction, an organic layer was extracted with toluene and dried with anhydrous sodium sulfate. After that, the resultant was purified with a silica gel column (mixed developing solvent containing heptane and toluene), whereby 0.518 g of Exemplified Compound 4 (yellowish white crystal) was obtained (60.1% yield).

Mass spectrometry confirmed 506.3 as the M+ of the compound.

Figure 6:
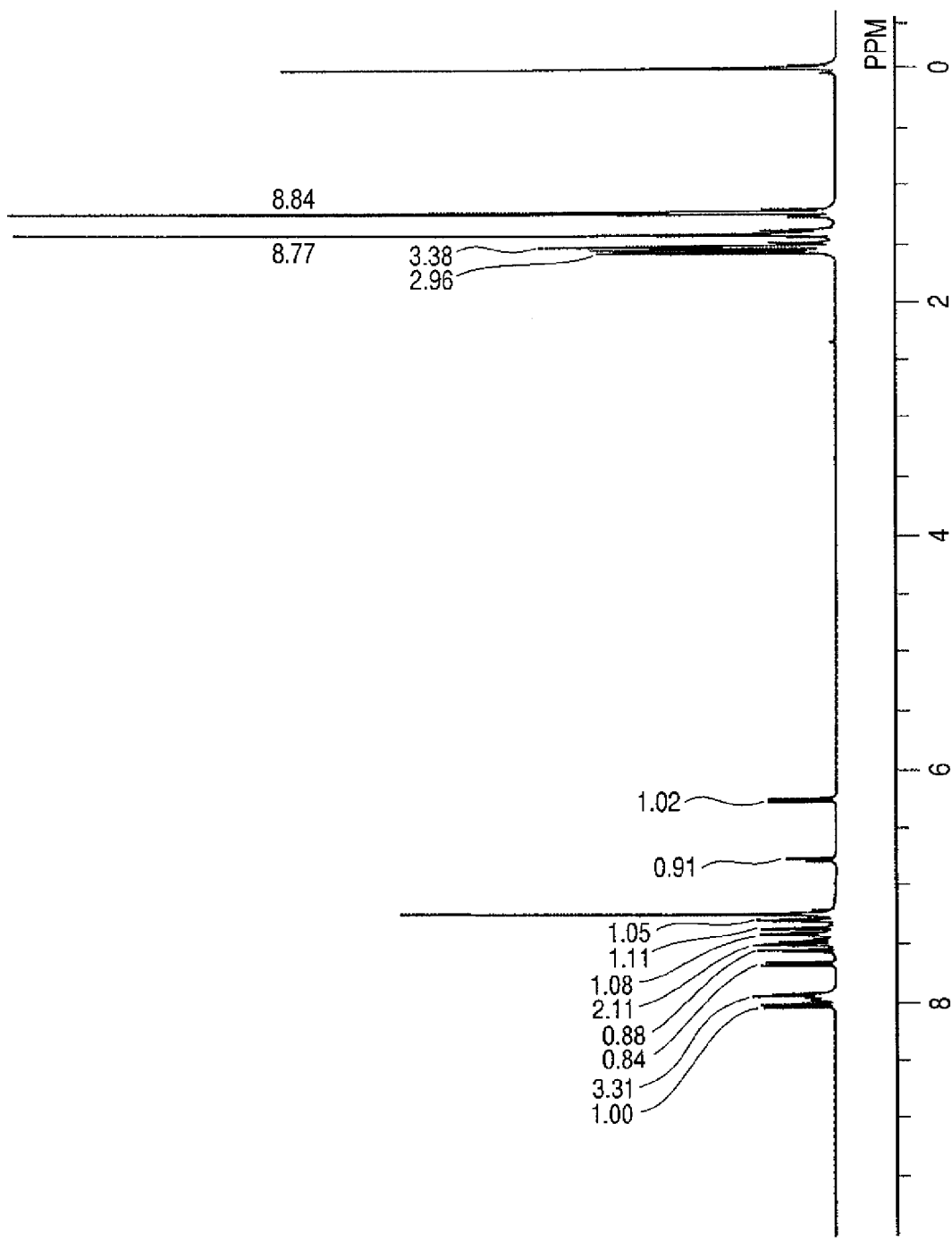
FIG. 6 is a $^1$HNMR chart of Exemplified Compound 4.

In addition, $^1$HNMR measurement identified the structure of Exemplified Compound 4 (FIG. 6). Further, differential scanning calorimetry (DSC) confirmed that the compound had a melting point of 287° C. and a glass transition point of 122° C.

In addition, the emission spectrum of the compound in a toluene dilute solution ($1 \times 10^{-5}$ mol/l) was such that strong light emission having a peak at 460 nm was observed.

EXAMPLE 2

Synthesis of Exemplified Compound 22

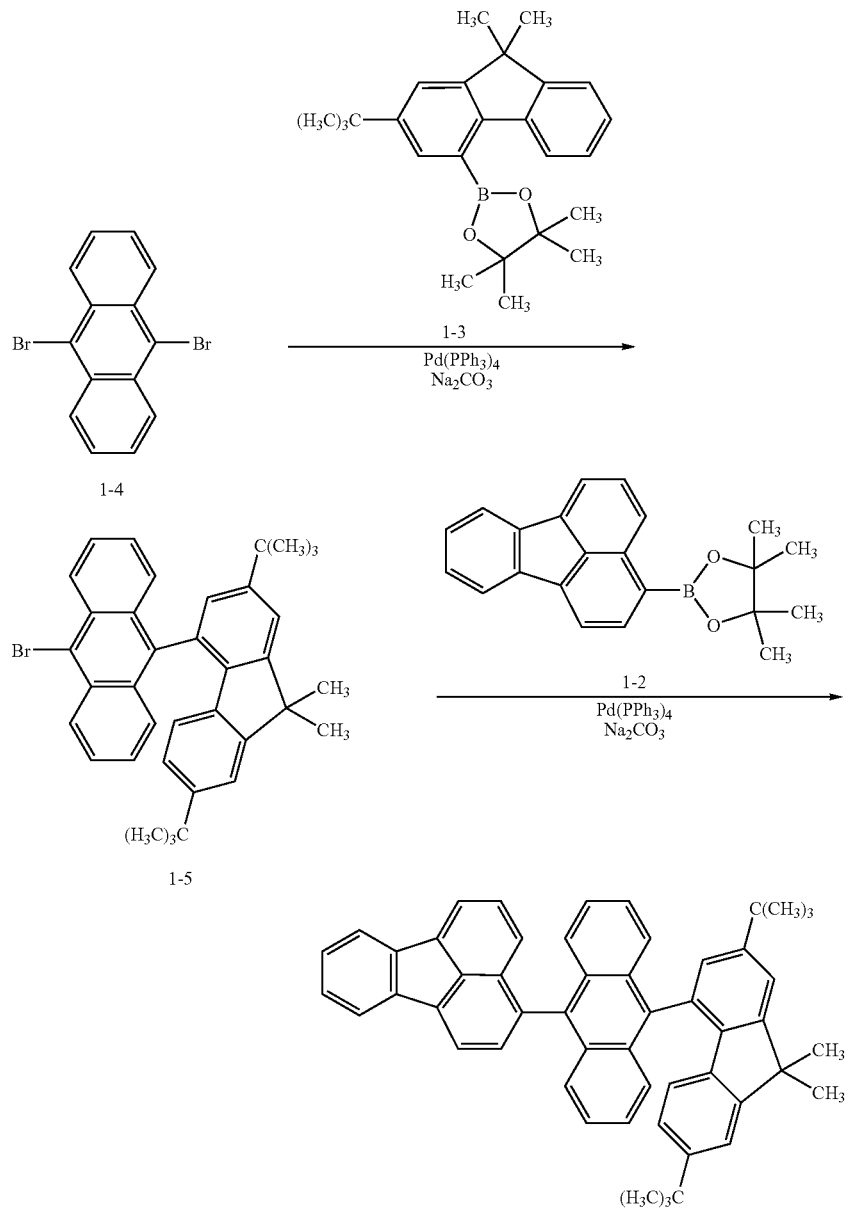

(a) Synthesis of Intermediate Compound 1-3

12.0 g (31.5 mmol) of Intermediate Compound 1-1, 1.70 g (3.15 mmol) of [1,3-bis(diphenylphosphino)propane]dichloronickel, 120 ml of toluene, and 20 ml of triethylamine were charged in a 200-ml three-necked flask, and the mixture was stirred under a nitrogen atmosphere at room temperature. During the stirring, 13.7 ml (94.5 mmol) of tetramethylpinacolborane were dropped to the mixture. The mixture was heated to 80° C., and was then stirred for 8 hours. After the reaction, the reaction solution was cooled to room temperature, 100 ml of a 1N aqueous solution of ammonium chloride were added to the reaction solution, and the mixed solution was stirred for 30 minutes. An organic layer was extracted with toluene and dried with anhydrous sodium sulfate. After that, the resultant was purified with a silica gel column (mixed developing solvent containing heptane and toluene), whereby 9.34 g of Intermediate Compound 1-3 (white crystal) were obtained (72.0% yield).

(b) Synthesis of Exemplified Compound 1-5

1.68 g (5.02 mmol) of Intermediate Compound 1-4, 2.31 g (5.52=mol) of Intermediate Compound 1-3, 80 ml of toluene, and 40 ml of ethanol were charged in a 200-ml three-necked flask, and the mixture was stirred under a nitrogen atmosphere at room temperature. During the stirring, an aqueous solution prepared by dissolving 1 g of sodium carbonate in 100 ml of water was dropped to the mixture, and then 0.579 g (0.502 mmol) of tetrakis(triphenylphosphine)palladium(0) was added to the mixture. The mixture was heated to 65° C., and was then stirred for 5 hours. After the reaction, an organic layer was extracted with toluene and dried with anhydrous sodium sulfate. After that, the resultant was purified with a silica gel column (mixed developing solvent containing heptane and toluene), whereby 1.84 g of Intermediate Compound 1-5 (yellowish white crystal) was obtained (65.1% yield).

Mass spectrometry confirmed 561 as the M+ of the compound.

(c) Synthesis of Exemplified Compound 22

1.10 g (1.96 mmol) of Intermediate Compound 1-5, 0.709 g (2.16 mmol) of Compound 1-2, 80 ml of toluene, and 40 ml of ethanol were charged in a 200-ml three-necked flask, and the mixture was stirred under a nitrogen atmosphere at room temperature. During the stirring, an aqueous solution prepared by dissolving 1.41 g of sodium carbonate in 100 ml of water was dropped to the mixture, and then 0.227 g (0.196 mmol) of tetrakis(triphenylphosphine)palladium(0) was added to the mixture. The mixture was heated to 77° C., and was then stirred for 5 hours. After the reaction, an organic layer was extracted with toluene and dried with anhydrous sodium sulfate. After that, the resultant was purified with a silica gel column (mixed developing solvent containing heptane and toluene), whereby 0.920 g of Exemplified Compound 22 (yellowish white crystal) was obtained (69% yield).

Mass spectrometry confirmed 715 as the M+ of the compound.

Figure 7:
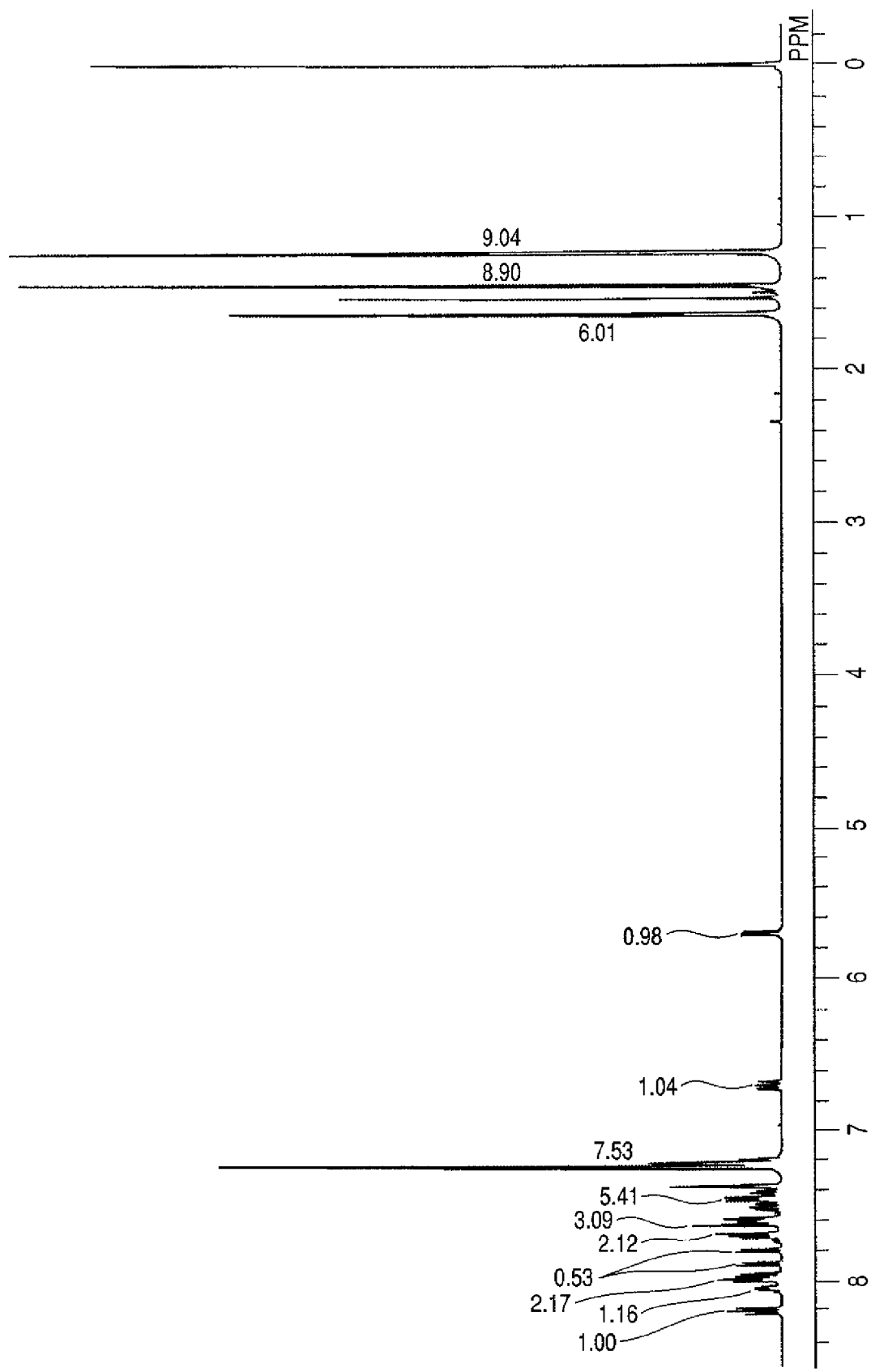
FIG. 7 is a $^1$HNMR chart of Exemplified Compound 22.

In addition, $^1$HNMR measurement identified the structure of Exemplified Compound 22 (FIG. 7). Further, differential scanning calorimetry (DSC) confirmed that the compound had a melting point of 287° C. and a glass transition point of 122° C.

In addition, as the emission spectrum of the compound in a toluene dilute solution ($1 \times 10^{-5}$ mol/l), strong light emission having a peak at 469 nm was observed.

EXAMPLE 3

Synthesis of Exemplified Compound 5

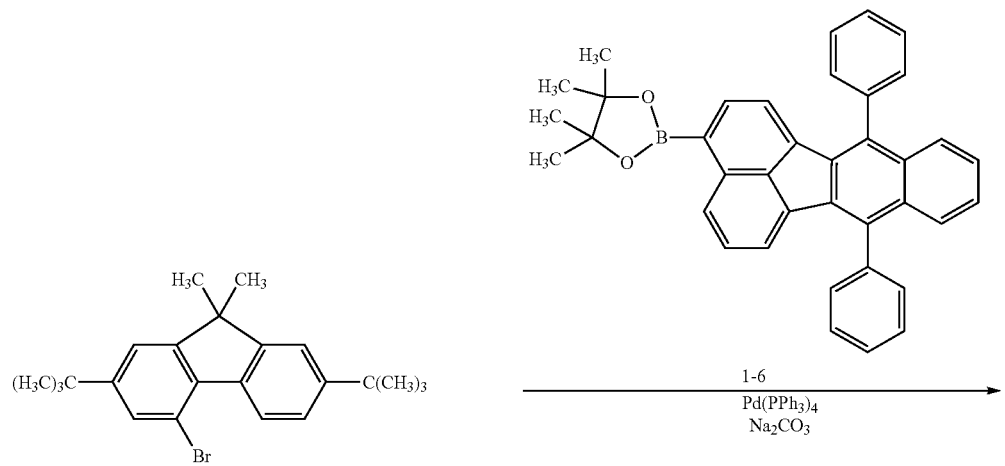

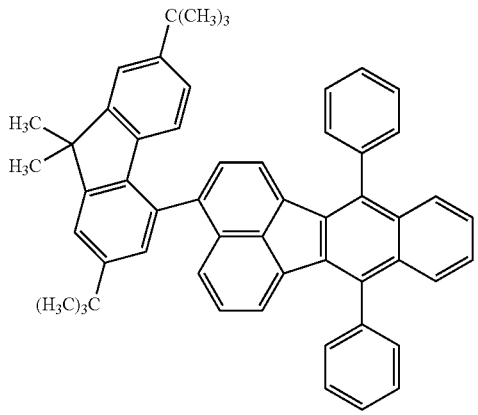

5

0.39 g (1.00 mmol) of Intermediate Compound 1-1, 0.530 g (1.00 mmol) of Compound 1-6, 10 ml of toluene, and 50 ml of ethanol were charged in a 100-ml three-necked flask, and the mixture was stirred under a nitrogen atmosphere at room temperature. During the stirring, an aqueous solution prepared by dissolving 10 g of sodium carbonate in 10 ml of water was dropped to the mixture, and then 0.06 g (0.05 mmol) of tetrakis(triphenylphosphine)palladium(0) was added to the mixture. The mixture was heated to 77° C., and was then stirred for 5 hours. After the resultant had been cooled to room temperature, the precipitated crystal was filtrated, and the resultant coarse crystal was recrystallized with toluene and ethanol, whereby 0.120 g of Exemplified Compound 5 (pale yellowish white crystal) was obtained (16.9% yield).

Mass spectrometry confirmed 708.4 as the M+ of the compound.

Figure 8:
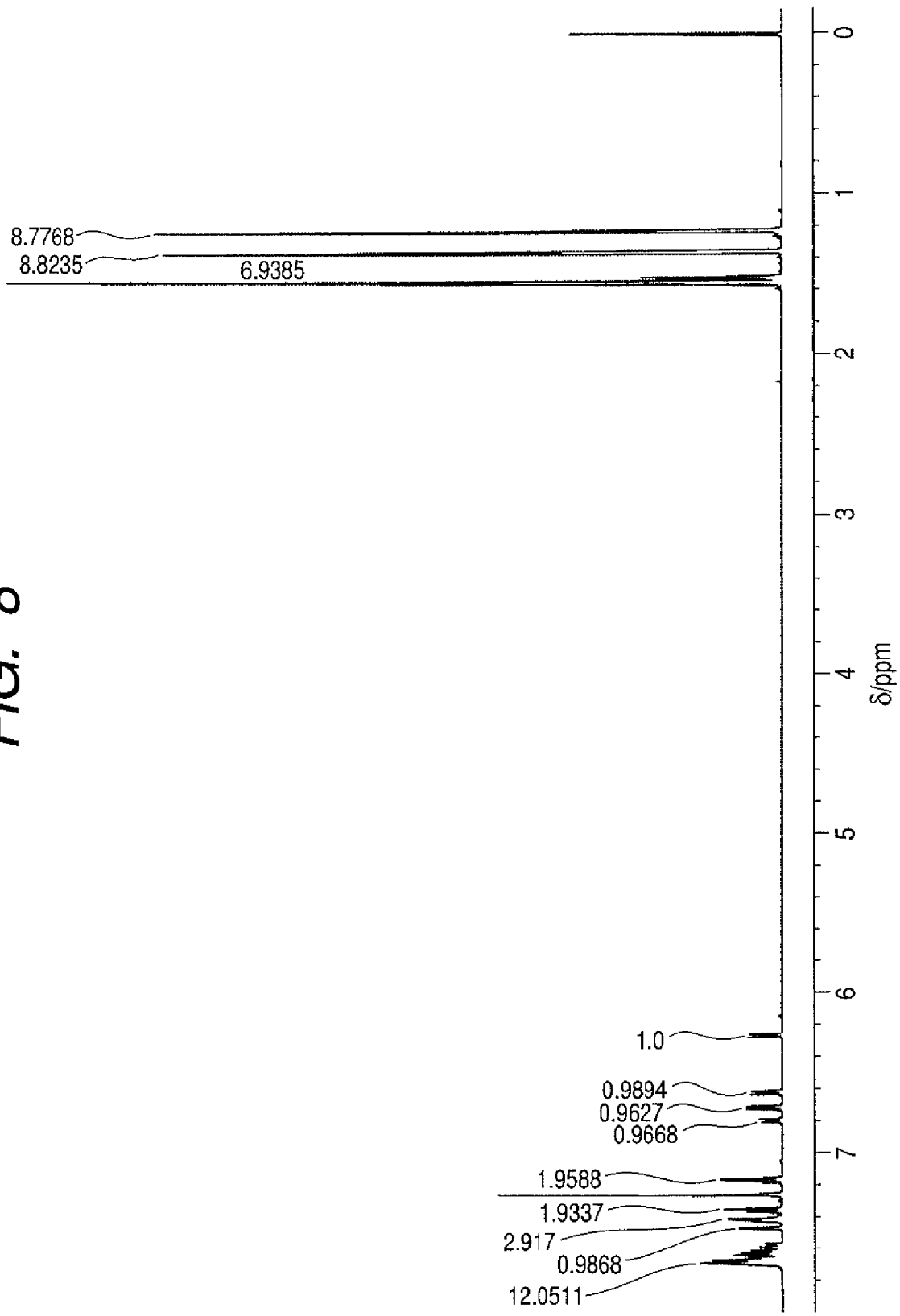
FIG. 8 is a HNMR chart of Exemplified Compound 5.

In addition, $^1$HNMR measurement identified the structure of Exemplified Compound 5 (FIG. 8).

In addition, as the emission spectrum of the compound in a toluene dilute solution ($1\times10^{-5}$ mol/l), strong light emission having a peak at 460 nm was observed.

EXAMPLE 4

An organic light-emitting device having the structure illustrated in FIG. 3 was produced by the method described below.

Indium tin oxide (ITO) as the anode 2 was formed as a film having a thickness of 120 nm on a glass substrate as the substrate 1 by a sputtering method, and the resultant was used as a transparent conductive supporting substrate. The resultant substrate was subjected to ultrasonic cleaning in acetone and isopropyl alcohol (IPA) in this order. Then, the substrate was cleaned in boiling IPA and dried. The substrate was further subjected to UV/ozone cleaning to be used as a transparent conductive supporting substrate.

A chloroform solution containing 0.1 wt % of a compound represented by the following structural formula 3-1 as a hole transport material was prepared.

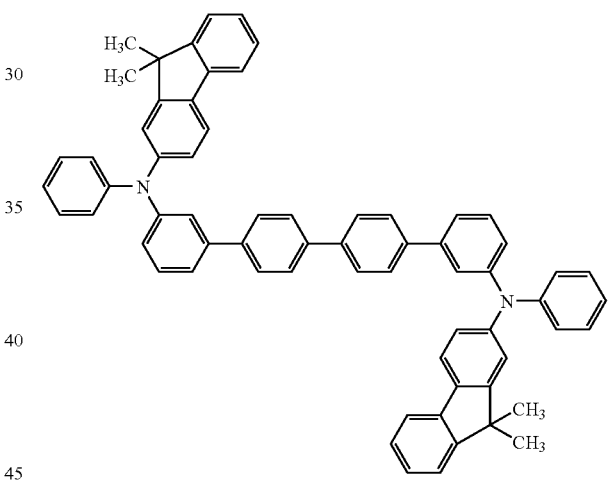

3-1

This solution was dropped onto the above-mentioned ITO electrode to form a film on the ITO electrode by spin coating at a revolving speed of 500 rpm for 10 seconds at first and then at a revolving speed of 1,000 rpm for 1 minute. Then, the substrate having the film on the ITO was placed in a vacuum oven at 80° C. and dried for 10 minutes, to thereby completely remove the solvent in the thin film. The thus-formed hole transport layer 5 had a thickness of 15 nm.

Next, the light-emitting layer 3 having a thickness of 40 nm was provided on the hole transport layer 5 co-depositing the above-described Exemplified Compound No. 4 as the first compound and the following structural formula 3-2 as the second compound (at weight ratio of 10:90). During the co-deposition, a degree of vacuum was $1.0\times10^{-4}$ Pa and a film formation rate was 0.2 nm/sec or more and 0.3 nm/sec or less.

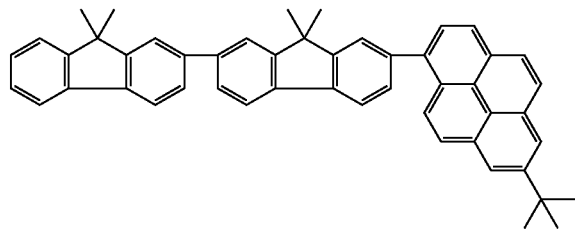

3-2

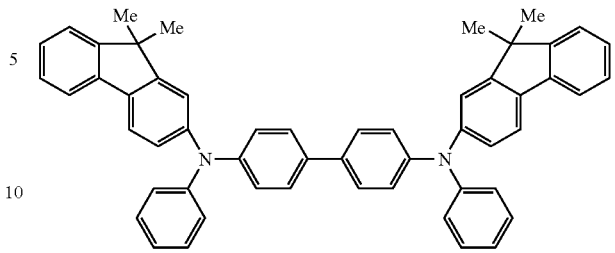

3-3

Further, the electron transport layer 6 having a thickness of 30 nm was formed by a vacuum deposition method using 2,9-[2-(9,9'-dimethylfluorenyl)]-1,10-phenanthroline. During the vacuum deposition, a degree of vacuum was $1.0 \times 10^{-4}$ Pa and a film formation rate was 0.2 nm/sec or more and 0.3 nm/sec or less.

Next, aluminum lithium (AlLi) having a thickness of 0.5 nm was formed on the obtained organic layer by a vacuum deposition method, and further an aluminum film having a thickness of 150 nm was formed thereon as the electron-injection electrode (cathode 4) by a vacuum deposition method, thereby producing an organic light-emitting device. A degree of vacuum during deposition was $1.0 \times 10^{-4}$ Pa. According to the condition of formation, a lithium fluoride film formation rate was 0.05 nm/sec, and an aluminum film formation rate was 1.0 nm/sec or more and 1.2 nm/sec or less.

The obtained organic EL device was covered with a protective glass and sealed with an acrylic resin adhesive material in a dry air atmosphere to prevent degradation of the device by adsorption of moisture thereon.

Under application of a voltage of 4 V to the thus-obtained device having the ITO electrode (anode 2) as a positive electrode and the Al electrode (cathode 4) as a negative electrode, blue light emission with an emission luminance of 450 cd/m$^2$ and emission efficiency of 2.8 μm/W was observed.

EXAMPLE 5

An organic light-emitting device having the structure illustrated in FIG. 4 was produced by the method described below.

A film of indium tin oxide (ITO) having a thickness of 120 nm was formed as the anode 2 on a glass substrate as the substrate 1 by a sputtering method, and the resultant was used as a transparent conductive supporting substrate. The resultant substrate was subjected to ultrasonic cleaning in acetone and isopropyl alcohol (IPA) in this order. Then, the substrate was cleaned in boiling IPA and dried in a vacuum oven at 120° C. The substrate was further subjected to UV/ozone cleaning to be used as a transparent conductive supporting substrate.

A chloroform solution containing 0.1 wt % of a compound represented by the following structural formula 3-3 as a hole transport material was prepared.

This solution was dropped onto the above-mentioned ITO electrode and formed into a film on the ITO electrode by spin coating at a revolving speed of 500 rpm for 10 seconds at first and then at a revolving speed of 1,000 rpm for 40 seconds. Then, the resultant was placed in a vacuum oven at 80° C. and dried for 10 minutes, to thereby completely remove the solvent in the thin film. The thus-formed hole transport layer 7 had a thickness of 15 nm.

Next, a compound represented by the following structural formula 3-4 was further vapor-deposited on the hole injection layer 7 to provide the hole transport layer 5 having a thickness of 15 nm.

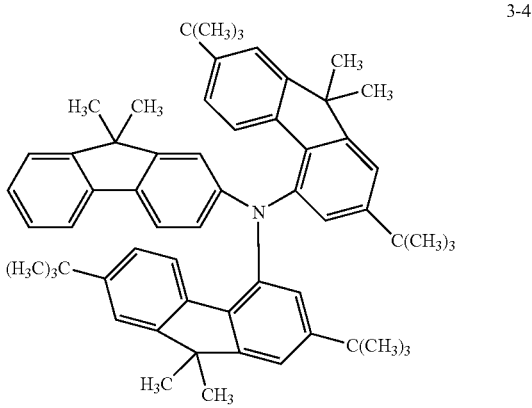

3-4

Further, Exemplified Compound 22 described above as a first compound and the compound represented by the structural formula 3-2 described above as a second compound were co-deposited (in a weight ratio of 5:95) on the resultant to provide the light-emitting layer 3 having a thickness of 30 nm. The layer was formed under conditions including a degree of vacuum at the time of the vapor deposition of $1.0 \times 10^{-4}$ Pa and a film deposition rate at the time of the vapor deposition of 0.1 nm/sec or more and 0.2 nm/sec or less.

Further, the electron transport layer 6 of 2,9-[2-(9,9'-dimethylfluorenyl)]-1,10-phenanthroline having a thickness of 30 nm was formed by a vacuum deposition method. A degree of vacuum during deposition was $1.0 \times 10^{-4}$ Pa and a film formation rate was 0.1 nm/sec or more and 0.2 nm/sec or less.

Next, a film of lithium fluoride (LiF) having a thickness of 0.5 nm was formed on thus-obatained organic layer by a vacuum deposition method, and an aluminum film having a thickness of 150 nm was further formed thereon through a vacuum deposition method, as the electron-injection electrode (cathode 4), thereby producing an organic light-emitting device. A degree of vacuum during deposition was $1.0\times 10^{-4}$ Pa. According to the condition of formation, a lithium fluoride film formation rate was 0.01 nm/sec, and an aluminum film formation rate was 1.0 nm/sec or more and 1.2 nm/sec or less.

The obtained organic EL device was covered with a protective glass and sealed with an acrylic resin adhesive material under a dry air atmosphere to prevent degradation of the device by adsorption of moisture thereon.

Under application of a voltage of 4 V to the thus-obtained device having the ITO electrode (anode 2) as a positive electrode and the Al electrode (cathode 4) as a negative electrode, blue light emission with an emission luminance of 104 cd/m$^2$ and emission efficiency of 4.9 μm/W was observed.

COMPARATIVE EXAMPLE 2

A device was produced in the same manner as in Example 4 except that Comparative Compound 4-1 shown below was used instead of Exemplified Compound 4, and the device was evaluated in the same manner as in Example 4. As a result, light emission from Exemplified Compound 4-1 could not be observed.

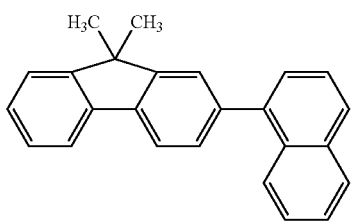

4-1

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2006-123784, filed Apr. 27, 2006, and 2006-310380, filed Nov. 16, 2006, which are hereby incorporated by reference herein in their entirety.

The invention claimed is:

1. A 4-arylfluorene compound represented by the following general formula (I):

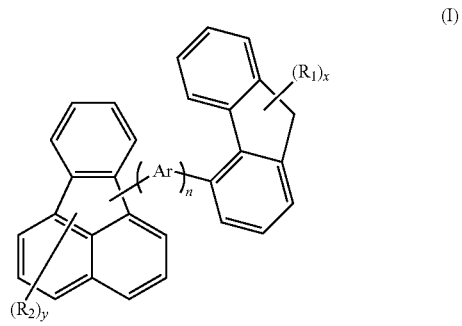

(I)

wherein n represents an integer of 1 to 10;
Ar represents a substituted or unsubstituted, divalent alkylene group, a substituted or unsubstituted, divalent aralkylene group, a substituted or unsubstituted, divalent arylene group, or a substituted or unsubstituted, divalent heterocyclic group;
each Ar may be the same as or different;
$R_1$ and $R_2$ each represent a substituted or unsubstituted alkyl group, a substituted or unsubstituted aralkyl group, a substituted or unsubstituted alkoxy group, a substituted or unsubstituted aryl group, a substituted or unsubstituted heterocyclic group, a substituted or unsubstituted amino group, a cyano group, or a halogen group, and $R_1$ and $R_2$ may be the same as or different from each other;
x and y each represent an integer of 0 to 9; and
when x or y represents an integer of 2 or more, $R_1$ groups or $R_2$ groups may be the same as or different from each other, or $R_2$ groups may be bonded to each other to form a ring.

2. A 4-arylfluorene compound according to claim 1, wherein Ar in the general formula (I) represents a substituted or unsubstituted phenylene group.

3. A 4-arylfluorene compound according to claim 1, wherein Ar in the general formula (I) represents a substituted or unsubstituted naphthalene group.

4. A 4-arylfluorene compound according to claim 1, wherein Ar in the general formula (I) represents a substituted or unsubstituted anthracene group.

5. An organic light-emitting device comprising:
a pair of electrodes comprising an anode and a cathode; and
an organic compound layer interposed between the pair of electrodes,
wherein the organic compound layer contains a 4-arylfluorene compound according to claim 1.

6. An organic light-emitting device according to claim 5, wherein the organic compound layer is a light-emitting layer.

* * * * *